(12) United States Patent
Goodnow et al.

(10) Patent No.: US 7,850,674 B2
(45) Date of Patent: Dec. 14, 2010

(54) GLUCOSE MEASURING MODULE AND INSULIN PUMP COMBINATION

(75) Inventors: Timothy T. Goodnow, Pleasanton, CA (US); Michael L. Blomquist, Blaine, MN (US); Jay G. Johnson, Maple Plain, MN (US)

(73) Assignees: Abbott Diabetes Care Inc., Alameda, CA (US); Deltec, Inc., St. Paul, MN (US)

( * ) Notice: Subject to any disclaimer, the term of this patent is extended or adjusted under 35 U.S.C. 154(b) by 0 days.

(21) Appl. No.: 12/239,022

(22) Filed: Sep. 26, 2008

(65) Prior Publication Data
US 2009/0082654 A1    Mar. 26, 2009

Related U.S. Application Data

(62) Division of application No. 10/458,914, filed on Jun. 10, 2003.

(51) Int. Cl.
*A61M 31/00* (2006.01)
*A61B 5/00* (2006.01)

(52) U.S. Cl. .................. 604/504; 604/67; 600/365

(58) Field of Classification Search .............. 600/365; 604/131, 504, 66, 67, 503, 65
See application file for complete search history.

(56) References Cited

U.S. PATENT DOCUMENTS

| | | | | |
|---|---|---|---|---|
| 5,376,070 | A | * | 12/1994 | Purvis et al. .............. 604/31 |
| 2003/0088238 | A1 | * | 5/2003 | Poulsen et al. .......... 604/890.1 |
| 2009/0069744 | A1 | * | 3/2009 | Goodnow .................. 604/66 |

\* cited by examiner

*Primary Examiner*—Kevin C Sirmons
*Assistant Examiner*—Catherine N Witczak
(74) *Attorney, Agent, or Firm*—Jackson & Co., LLP

(57) ABSTRACT

A combination glucose measuring and insulin pumping device is described. The two major components, a glucose measuring module and an insulin pump, are held together by a quick attach and release mechanism. Communication between the glucose measuring module and the insulin pump is by a wireless modality. The glucose measuring module determines the glucose level in a sample, and wirelessly transmits the data to the insulin pump, where the data are stored in a memory, and are available for visual display on the insulin pump, and for incorporation into selection of appropriate protocols for the rate of insulin infusion by the pump into the patient.

21 Claims, 3 Drawing Sheets

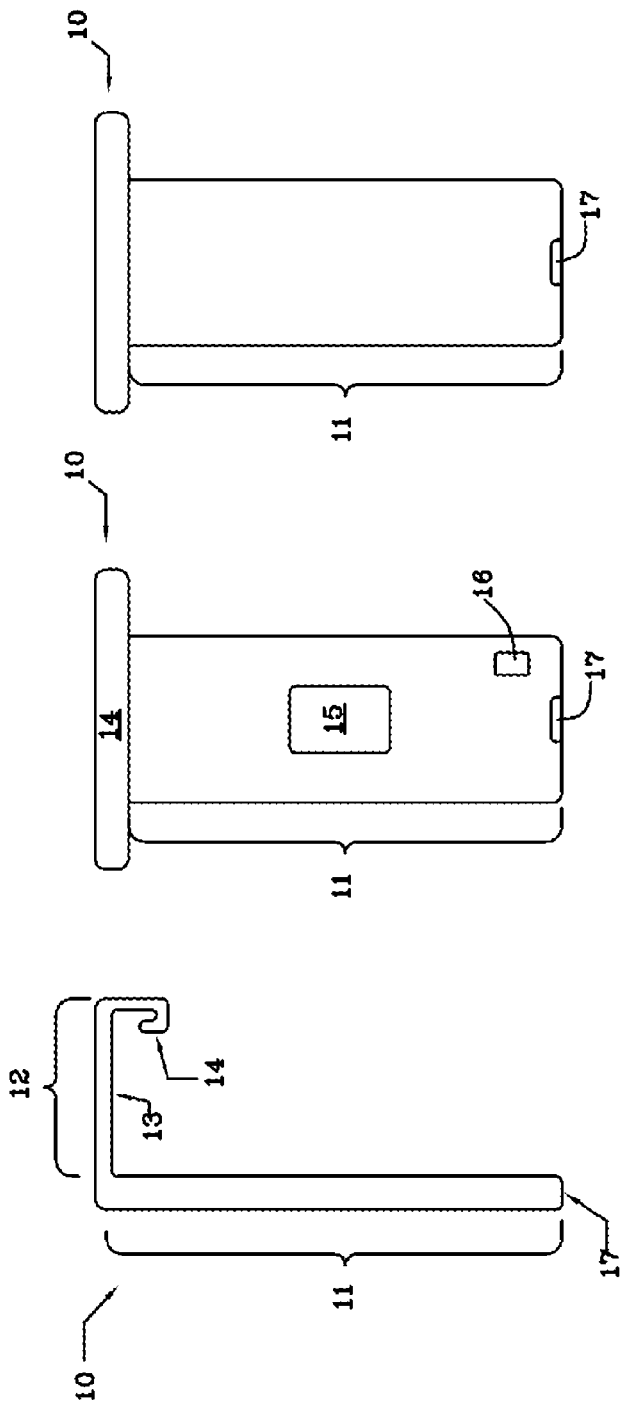
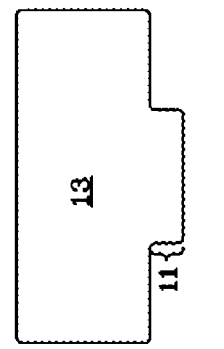
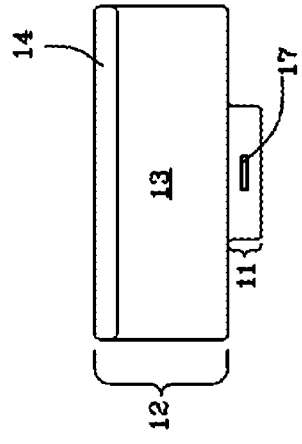
FIG. 1A  FIG. 1B  FIG. 1C  FIG. 1D  FIG. 1E

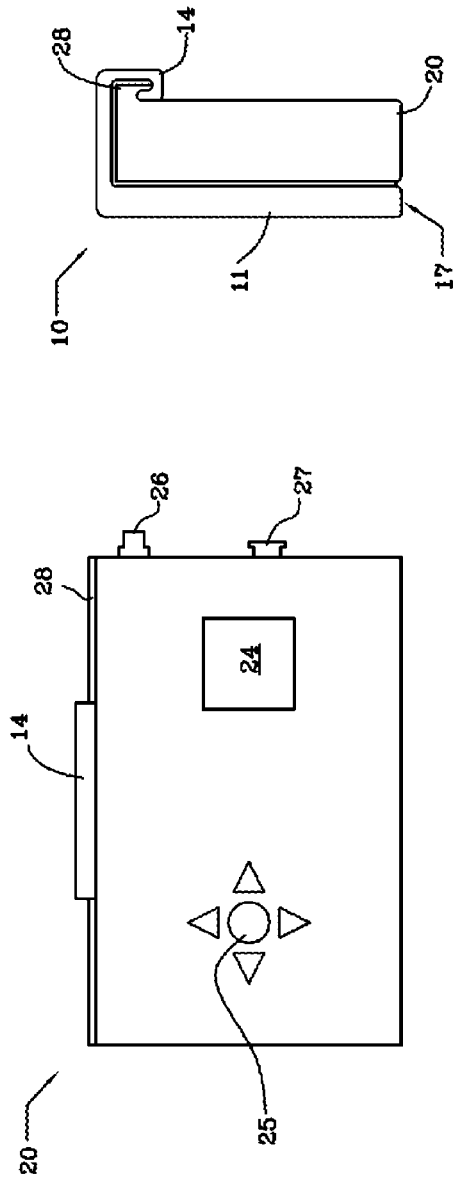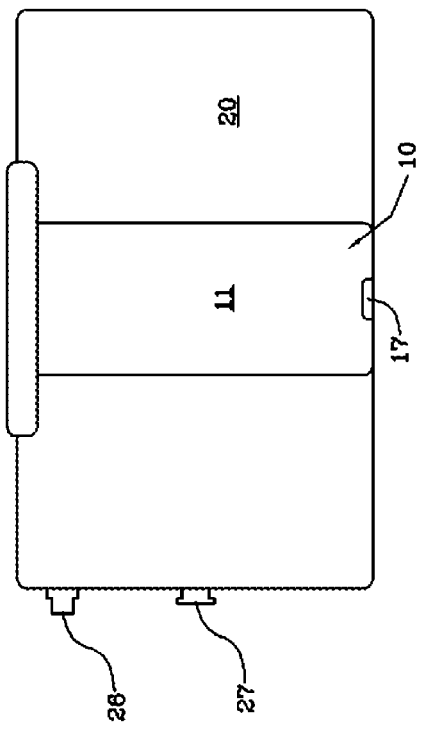

GLUCOSE MEASURING MODULE AND INSULIN PUMP COMBINATION

RELATED APPLICATIONS

This Application is a divisional application of pending U.S. patent application Ser. No. 10/458,914 filed on Jun. 10, 2003, entitled "Glucose Measuring Module And Insulin Pump Combination," the disclosure of which is incorporated herein by reference for all purposes.

FIELD OF THE INVENTION

This invention relates to a device and method by which a glucose reading from a detachable portable glucose sensor module can be wirelessly delivered to an insulin pump on which the module is mounted.

BACKGROUND

The number of diagnosed cases of diabetes continues to increase in the U.S. and throughout the world, creating enormous economic and public health consequences. Devices and therapies that improve the quality of life for the diabetic patient thus are important not only for the patient, but for society at large. One area in which recently developed technologies have been able to improve the standard of care has been in the maintenance of tight control over the blood glucose levels. It is well known that if a diabetic patient's blood glucose values can be maintained in a relatively narrow and normal range of from about 80 milligrams per deciliter (mg/dL) to about 120 mg/dL, the physiologically damaging consequences of unchecked diabetes can be minimized. With better blood glucose information, diabetic patients can better exercise tight control of their blood glucose level through a variety of means, including diet, exercise, and medication. For this reason a large industry has developed to provide the diabetic population with ever more convenient and accurate ways to measure blood glucose. There are many forms of these measuring devices; one common type is represented by hand-held electronic meters which receive blood samples via enzyme-based "test strips". In using these systems, the patient lances a finger or alternate body site to obtain a blood sample, the strip is inserted into a test strip opening in the meter housing, the sample is applied to the test strip and the electronics in the meter convert a current generated by the enzymatic reaction in the test strip to a blood glucose value.

Some diabetic patients require insulin for the treatment of their diabetes, in order to maintain their glucose levels within the desired range. These "insulin-dependent" diabetic patients have traditionally administered insulin doses to themselves via a hypodermic syringe or with a specialized injector known as an "insulin pen". Although these injection methods can deliver insulin at an appropriate time and at an appropriate total dosage, the single bolus aspect of the delivery is unlike a physiological profile of insulin production in the body, which involves a lower rate of insulin entry into the bloodstream, over a more extended time course. A more recently available technology is represented by insulin pumps. These devices offer significant therapeutic value as they deliver insulin in a more physiological manner, with measured doses of insulin being infused slowly, over an extended period of time. Further, the rate at which insulin is delivered can be programmed to follow standard or individually-modified protocols, to give the user even better glucose control over the course of a day. Insulin pumps have commercially evolved to become small in size, which offers easier portability and unobtrusiveness, and with electronic advances, they have evolved to become more fully-featured, and thereby capable of enhanced performance. These various advantages in terms of health care quality and user convenience have supported the growth of the insulin pump market.

Diabetics and especially insulin pump users typically carry with them a strip-and-meter glucose test kit at all times, so they can ascertain their blood glucose level during their day. It has been recognized that combining the newer technologies of insulin administration with the newer technologies of glucose measurement could provide user convenience. Such an integrated combination is shown in U.S. Pat. No. 5,665,065, which teaches that the mechanism for measuring blood glucose can be built into the housing of an insulin pump. This patent further teaches that the combined glucose measuring and pump system can permit the user to (1) obtain a glucose value, (2) input the glucose value to the microprocessor based electronics within the pump housing, (3) direct the electronics to calculate a recommended modification to the default or currently in-use insulin delivery protocol, and (4) select either the newly recommended protocol or the original default insulin delivery protocol.

While the advantages of such glucose measuring/insulin pump combinations have been known in the patent literature for many years, in fact, no such device has become commercially available. One fundamental reason for this concept remaining unrealized in the market may involve the now standard and expected watertight feature of the pump, which allows the pump user to shower and swim without removing the pump. On the other hand, waterproofing of a glucose strip testing device is inherently problematic, as the strip port itself is a necessary open connection between the space within the glucose sensing device and the external environment. Thus, the full integration of glucose strip test functionality into an insulin pump would remove the desirable watertight feature of the pump. Such would be the case with a device according to the type shown in U.S. Pat. No. 5,665,065, which if exposed to a wet environment, would allow the entry of water through the test strip opening in the pump housing, where the water could damage the electronics and/or mechanical portions of the pump.

Other practical factors may also contribute to the failure of a combination device to enter the market. Insulin pumps, though expensive, are becoming well established in the market. Pump users tend to remain loyal to their initial choice. Glucose meters, in contrast, are less expensive to acquire (they are often provided to users without charge), and users more often switch between meter brands. Thus, in designing such an integrated combination device, a pump manufacturer would need to commit to particular blood glucose measuring technology in the face of the concern that such technology could become less competitive or even obsolete during the normal life of the pump product. Finally, pump manufacturers are very aware that pump users are interested in pumps that are small and unobtrusive. Clearly, combining two devices can only increase the size of the pump housing, thus making the pump potentially less attractive in a market that has become used to the idea that smaller is better.

In view of these various technical factors associated with the therapeutic devices and the market considerations, it would be desirable to provide an insulin pump user the benefits and performance of a functionally combined glucose measuring device and insulin pump in a configuration that nevertheless avoids the practical disadvantages associated with a physical integration.

SUMMARY OF THE INVENTION

A combination glucose measuring and insulin pumping device in which two major components, a glucose measuring module and an insulin pump, are held together by a quick attach and release mechanism. Communication between the glucose measuring module and the insulin pump is by a wireless modality. The glucose measuring module determines the glucose level in a sample, and wirelessly transmits the data to the insulin pump, where the data are stored in a memory, and are available for visual display on the insulin pump, and for incorporation into selection of appropriate protocols for the rate of insulin infusion by the pump into the patient.

The invention features a glucose measuring module that includes glucose measuring circuitry preferably for enzymatic electrochemical detection of glucose in a blood sample. The module includes a quick attach and release clasp permitting the user to readily attach and detach the module from an insulin pump housing. The module further includes circuitry for wirelessly transmitting data related to the glucose values determined in the module to the attached insulin pump, for example by infrared radiation. The module can be inexpensively manufactured since it need not include a display or control buttons, but can, instead, rely on the controls and display on the insulin pump.

BRIEF DESCRIPTION OF THE DRAWINGS

The invention will now be described by reference to the figures, wherein like reference numerals and names indicate corresponding structure throughout the several views.

FIGS. 1A-1E show the glucose measuring module of the invention in a side view, front view, back view, bottom view, and top view, respectively.

FIGS. 3A-3C show the combined glucose measuring module and insulin pump housing combination in a front view, side view, and back view, respectively.

DETAILED DESCRIPTION

Figure 2:
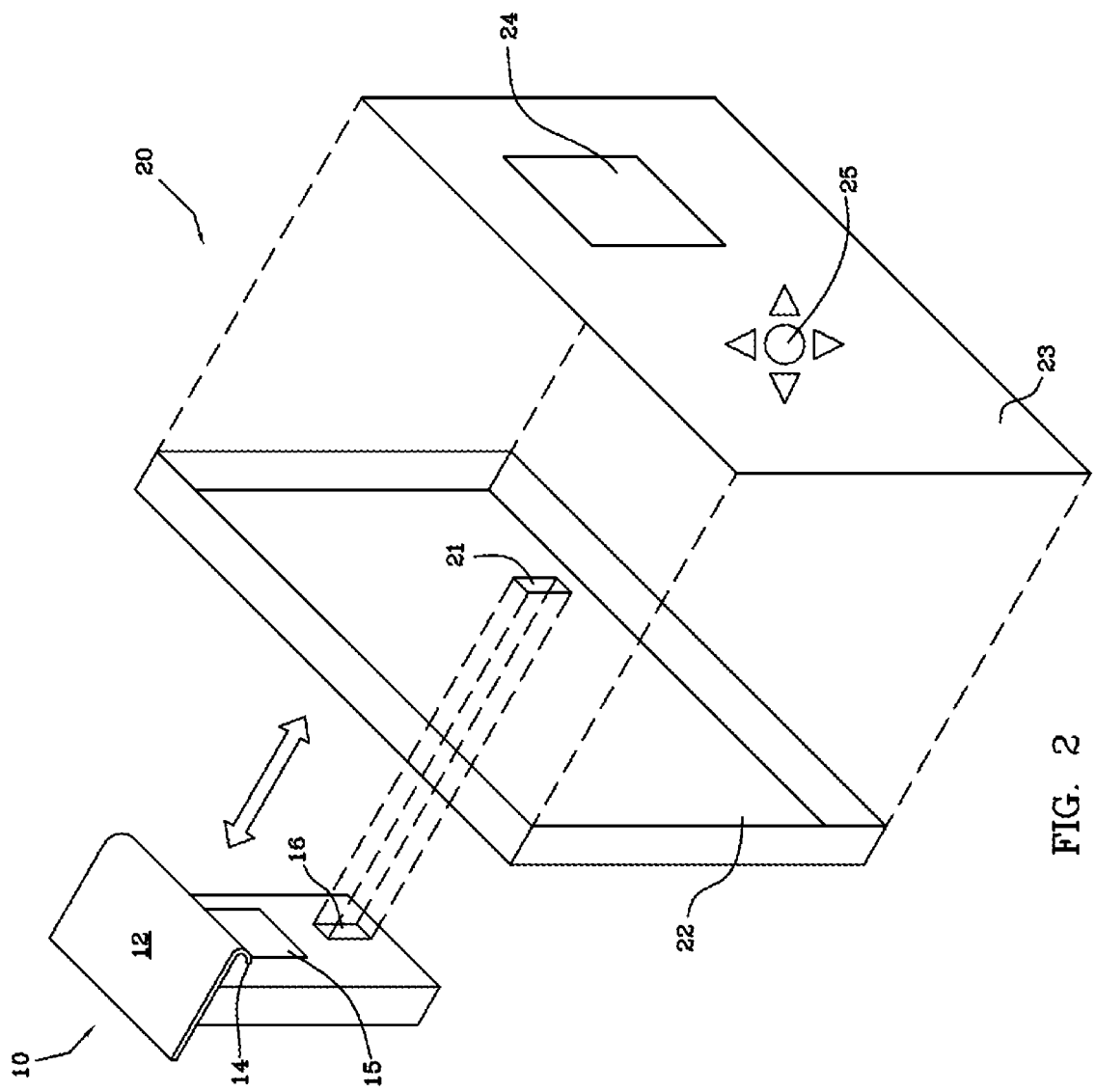
FIG. 2 shows a perspective view of the glucose measuring module separate from, but in relation to, an insulin pump housing. In this view the insulin pump housing is shown exploded forward from the back of the housing to expose an interior side of the back wall.

The present invention is a device resulting from the functional combination of a glucose measuring device and an insulin pump, wherein the device and pump are connected by a quick attach and release mechanism. By way of an overview of the figures, FIGS. 1A-1E depict the glucose measuring device or module portion of the combination in various views; FIG. 2 depicts the glucose measuring component and the insulin pump component device aligned with respect to each other as they are positioned for attachment together; and FIGS. 3A-3C depict the two major device components, the glucose sensor and the insulin pump housing, in their mutually attached or coupled configuration, in various views.

In the invention, the glucose measuring device determines a user's glucose level (typically from a sample of blood), and wirelessly transmits that information to the insulin pump. The insulin pump, in turn, receives the wirelessly transmitted data, and through a microprocessor, places the data in memory for storage, and from the memory the data can be sent to a display, and/or can be utilized in controlling the performance of the pump. By way of noting design requirements and constraints on the invention, it is important that the glucose measuring device portion of the invention is as small as possible, and specifically shaped in such a way as to minimize the size of the combined measuring device and pump combination. It is within the scope of the invention that the measuring device, in a preferred embodiment, need not include a display. In this manner the device can be less expensively manufactured, and its size minimized. However, in combination with the pump, the data delivered to the pump from the measuring device can be displayed on the existing pump display. While the module need not include a large or expensive display, it may nevertheless be advantageous to include some ability to advise the user of a glucose level which is determined when the module is used as a "standalone" unit. For example, the module could include a very low cost, small three digit LCD display. Alternatively, the module could include LED indicator lights (e.g. red for out of desired range, green for within desired range).

FIGS. 1A-1E depict a glucose measuring module 10 comprising a glucose sensor housing 11 and a quick attach/quick release clasp 12. The clasp can be made of a variety of materials, including metal or plastic, or parts including both. In a preferred form, clasp 12 includes an extension portion 13, which portion extends across the top of an insulin pump housing (as seen in FIGS. 2 and 3), and a lip/connector portion 14.

FIG. 1A shows the glucose measuring device in a side view and highlights the thin profile of housing 11. Test strip port 17 can also be seen at the bottom of the module. Clasp 12 is seen in this embodiment to be integrated with and contiguous with the glucose sensor housing 11. Alternatively, all or a portion of clasp 12 can form part of the insulin pump housing and nevertheless form a connection with housing 11 when module 10 and the insulin pump housing are brought together. In yet another form of the invention, clasp 12 can be a part separate from, but attachable to, both module housing 11 and the insulin pump housing.

Glucose sensor housing 11 contains any glucose sensing system of the type well known in the art that can be configured to fit into a small and preferably thin profile. Such a system can include, for example, the electrochemical glucose strip and meter sensing system sold by TheraSense, Inc. of Alameda, Calif. under the FreeStyle® brand, or other strip and meter glucose measuring systems. The housing thus encompasses the sensor electronics and strip connector (not shown), which connector is accessed via test strip port 17. Housing 11 will typically also include a battery or batteries which are accessed via battery door 15. In a preferred form of the invention, housing 11 includes a wireless data transmission port 16. Battery door 15 and data transmission port 16 have outer surfaces that are smoothly aligned with a matching surface of the housing, as shown in FIG. 1B (and the profile of FIG. 1A), so that housing 11 fits in an aligned fashion with the insulin pump housing to which it will be attached.

It is not necessary that the combination of the invention include a port for the transmission of infrared radiation, for example the data to be sent from the glucose sensing module to the pump can be transmitted by other known communications protocols such as BlueTooth, IEEE 802.11b or other wireless protocols. It is important in the invention, however, that the data be sent in a manner that avoids having a "hard" or wired connection between the module and the pump housing so that it is not necessary to have a potentially water accessible opening in the pump housing. That is, the invention is most advantageously used with a pump having a housing that is "closed" in the sense that it is at least water-resistant and preferably is water-proof.

As will be described in detail below, the glucose sensing system in housing 11 is electronically activated by connection of a glucose test strip to the glucose sensing system via test strip port 17. Alternatively, the sensing system can be activated by on/off buttons that can be incorporated into the housing as is common with glucose meters. However, the preferred embodiment depicted in FIGS. 1-3 does not have manual control buttons on the glucose sensing module housing. Thus, in this embodiment, control of the function of the glucose sensing module is undertaken via the user accessible control buttons on the pump housing in combination with the pump and module microprocessors.

In a front view (FIG. 1B) of glucose measuring module 10, the relative width and breadth of housing 11 is evident. Shown on the inner or front face of housing 11 are battery door 15 and wireless data transmission port 16. The wireless transmission mode in this embodiment is infrared (IR). In a back view (FIG. 1C) of glucose measuring module 10, the shape of housing 11 and extension portion 13 of quick attach and release clasp 12 is shown. The bottom view of FIG. 1D of module 10 shows the position of strip port opening 17 relative to housing 11. FIG. 1E shows the upper aspect of sensor housing 11 as it connects with extension portion 13.

Clasp 12 is of a quick attach and release type for detachably coupling glucose measuring module 10 to insulin pump housing 20 (see FIG. 2 below). Terms synonymous to "quick attach and release" include "quick-connect", "snap-on", "snap-fit" and "click-on". The connection afforded by clasp 12 has a mechanical stability that is sufficient to ensure that the two component devices remain coupled during normal use, and sufficient to maintain the stability and alignment of the IR wireless connection between data transmission port 16 of the module and an IR data receiver port 21 of the insulin pump. The attachment and detachment of these components via the clasp is of a quick and simple nature, requiring neither tools nor manual exertion beyond finger force to effect. Further, preferably, the connection and disconnection steps are each single-action in nature; connection need not be followed by a locking step, nor is disconnection preceded by any required unlocking step.

In the presently described and illustrated embodiment, clasp 12 is integrally associated with the glucose sensor module 11, and it actively clasps insulin pump housing 20. As mentioned, however, the clasp can instead be integrally associated with pump housing 20, from which position it clasps module 11. Alternatively, the clasp can be a stand-alone piece, integrally associated with neither the glucose sensor module nor the insulin pump, but capable of clasping and binding the two component devices together. The depicted clasp embodiment and the alternatives described are but examples of numerous variations of quick attach and release mechanisms that are well known in the art, and would be functionally equivalent to the examples illustrated and described herein. For example, it may be useful to use protrusions on pump housing 20 for engagement of the module/clasp. In particular, one or both of the fitting for the insulin infusion set and the battery cap (shown as 26 and 27 in FIG. 3, respectively) may be used as anchors for such engagement.

Returning to the figures in sequence, FIG. 2 shows the combination glucose measuring device and insulin pump, exploded and in a perspective view, with the internal mechanisms and electronics of the pump not appearing for clarity. An embodiment of glucose sensor module 10 and an exemplary insulin pump housing 20 are shown obliquely from their front, aligned in their mutually attached configuration, but exploded outward from each other. From this front view perspective, battery receptacle door 15 and IR transmission port 16 of glucose module 10 are visible, as well as clasp 12 with its extension portion 13 and lip portion 14. Insulin pump housing 20 includes a back wall 22 and a front or face wall 23. This view shows the back and front walls exploded apart from each other in order to expose the interior aspect of back wall 22, thus showing the position of wireless data receiver port 21 contained therein. It is further illustrated in FIG. 2 that wireless data transmission port 16 of glucose sensor module 10, and the wireless data receiver port 21 on insulin pump housing 20 are physically aligned in a manner such that when the glucose sensor module and the insulin pump are clasped together in the configuration of the combined device that the two wireless ports are directly facing each other. Such direct alignment is appropriate in order to support robust wireless transmitting and receiving of data in the IR spectral range.

Visible on the front face wall of housing 20 are visual display 24, and pump control buttons 25. These control buttons are also used to manage the glucose sensor module as well, when the module is clasped to the housing and in alignment for IR communication. Though wireless communication can be accomplished via means (such as BlueTooth) that do not require such alignment, the present embodiment must have a clasp that ensures such alignment. This can be accomplished by including limits or "stops" (not shown) to the width of the lip engaging portion 28 on housing 20 to which lip 14 of module 10 engages, so as to permit attachment of the module only in a position in which there is alignment.

Insulin pump housing 20 is preferably "watertight," to protect the internal mechanisms and electronics from the damaging effects of water. "Watertightness" refers to the prevention of water ingress into an article or piece of equipment under various conditions of water exposure. To quantify the degree of watertightness, the Japanese Industrial Standards and the British Standards both use a scale that ranges from "0" to "8", and the definitions of each level in both systems are very similar to each other. To clarify, what is being quantified is the level of water exposure, not the degree to which water is excluded (which is absolute). The watertightness of the insulin pump housing is preferably in compliance with level 8 of both the Japanese and British standards. Thus, "JIS 8" (Japanese Industrial Standards) and "IPX8" (British Standards Institute, Water Intrusion Standards) define watertightness in a submersion context, i.e., the equipment excluding water while being continually submerged (or immersed) in water for periods of time and at depths or pressures that are specified by the manufacturer. A typical level 8 specification for the watertightness of an insulin pump housing is, for example, watertightness when submerged to a depth of 8 feet for 30 minutes, or to a depth of 12 feet for 3 minutes.

FIGS. 3A-3C show the combination glucose measuring module and insulin pump in a front view (FIG. 3A), side view (FIG. 3B), and back view (FIG. 3C). The front view shows the functional or interactive face of the insulin pump, where visual display 24 and control buttons 25 are located. These display and control elements represent the device user interface, where the diabetic patient can view glucose sensor information, and control the performance of the insulin pump and the glucose sensing system. On one lateral side of the pump, in this embodiment, is a fitting 26 for an insulin infusion line, as is well known, and a screw type battery cover 27. Visible in the front and side views is lip engaging portion 28. Side view (FIG. 3B) is redundant of FIG. 1A with respect to the glucose measuring module 10, but shows insulin pump housing 20 also, as well as the attached or coupled form of the combined glucose module and insulin pump. The back view (FIG. 3C) shows the back of glucose measuring module 10 in the foreground, and the back of the insulin pump 20 in the background. Glucose sensor module 10, the module's strip port 17, and the clasp portion of the glucose measuring device are apparent, as depicted earlier in FIG. 1C. Visible on the left side of pump housing 20, in this back view, is fitting 26 for the insulin infusion line as well as battery cover 27, as was shown also in FIG. 3A.

With regard to the wireless communication between glucose measuring module 10 and the insulin pump, as noted above, the modality is infrared (IR) light, preferably transmitted using IrDA Data Protocols. This modality is appropriate for high-speed, short-range, line-of-sight, point-to-point wireless data transfer. Features of infrared data transmission are well described on the website of the Infrared Data Association (http://www.irda.org/), IrDA Data defines a standard for an interoperable universal two-way wireless IR transmission port. The technology is widespread, being installed within move than 300 million electronic devices, many of which are of the portable or handheld variety, including insulin pumps such as the Deltec Cozmo™ pump, made by Deltec, Inc. (St. Paul, Minn.).

In the context of the present invention, to review, wireless data are transferred between the glucose measuring module via data transmission port 16 and data receiver port 24 of the insulin pump, which are aligned in close apposition when the glucose measuring module and the insulin pump are attached together in the configuration of the invention. These data ports are two-way transceivers, they are termed "transmission" (in the case of the glucose measuring module port) and "receiver" (in the case of the insulin pump) because of the predominant direction of signal flow, which is from the glucose measuring module to the insulin pump. In practice, however, there is transmission of some information back from the insulin pump to the glucose measuring module, which is important particularly in establishing a secure, mutual, and specific recognition between the individual components.

In practice, the inventive combination glucose measuring and insulin pump device is operated in the manner now to be described briefly. A typical user of this invention would be an insulin dependent diabetic, who is using an insulin-infusion pump, and who checks his or her blood glucose level multiple times per day. First, the patient assures that the glucose measuring device and the insulin pump are properly attached or coupled to each other, and then inserts a glucose test strip into strip port 17 of glucose measuring module 10. Within the glucose measuring module, the connection of the strip with a glucose strip connector (not shown) provides an electrical connection between the strip and the internal electronics of the module. Upon such contact between the glucose strip and the glucose strip connector, software within the module and pump is activated (either without specific user interaction via connection between conductive portions of the strip and the connector, or manually using control buttons 25 on the pump) in order to be ready to receive electrical data from the glucose test strip. Activation of the glucose measuring module causes electronics within the module to transmit a signal through the wireless transmission port 16, which is, in turn, received through the data receiver port 24 of the insulin pump, and such activation is noted on display 24 of the pump. The opposite end of the glucose strip remains protruding out from the glucose module.

Next, the patient obtains a small volume blood sample through the use of a skin puncturing device or lancet. Details of the operation of the lancet and the glucose level determining procedures are well described in U.S. Pat. Nos. 6,143,164 and 6,338,790, incorporated herein by reference. The patient then brings an exposed edge of the glucose test strip into contact with the blood drop that has appeared at the lancet puncture site, and the blood moves into a sample chamber within the glucose strip. Electronic mechanisms within the test strip sense when a sufficient sample volume is contained within the sample chamber, a signal is wirelessly transmitted from the glucose measuring module to the insulin pump, as described above, and a notice of this sufficient volume then appears on the display of the insulin pump. Electrochemical processes within the glucose test strip then proceed to determine the level of glucose in the sample, and such data is, in turn, wirelessly transmitted from the glucose module to the insulin pump, where the data is stored in an electronic memory, is displayed on the insulin pump display, and is available for retrieval at a later time and/or available for entering into other electronic processes that control the function of the insulin pump. Upon completion of data transfer, as indicated by information appearing on the pump display, the user withdraws the glucose test strip and discards it. According to particulars of the pump type and manufacturer, and particular methods of pump use, the user can then proceed to make use of the glucose data within the larger context of his or her medical care.

The invention has been described with reference to various specific and preferred embodiments and techniques. It will be apparent, however, to one of ordinarily skill in the art that many variations and modifications may be made while remaining within the spirit and scope of the invention.

What is claimed is:

1. A method of measuring the glucose level of a diabetic using a modular glucose measuring module and insulin pump combination comprising:
    (a) attaching a glucose measuring module without a display to an insulin pump housing using a mechanical clasp comprising a quick attach and release mechanism, the attaching including engaging a lip of the quick attach and release mechanism with a lip-engaging portion of the pump housing to align the insulin pump housing with the glucose measuring module;
    (b) inserting a glucose test strip in the module;
    (c) contacting the glucose test strip to a blood sample;
    (d) determining data relating to a glucose value based on said sample using a microprocessor in the module;
    (e) transmitting said data wirelessly from said module to said insulin pump and converting said data to a glucose value using a microprocessor in said pump;
    (f) displaying said glucose value on a display on said pump; and
    (g) detaching the clasp and module from the pump housing.

2. The method of claim 1 wherein the insulin pump housing is watertight.

3. The method of claim 1 including activating the glucose measuring module when the glucose test strip is inserted.

4. The method of claim 3 wherein activating the glucose measuring module includes transmission of a signal to the insulin pump.

5. The method of claim 4 wherein the signal is displayed on the display of the pump indicating activation of the glucose measuring module.

6. The method of claim 1 including controlling one or more functions of the glucose measuring module using a control button provided on the insulin pump housing.

7. A method of measuring the glucose level of a diabetic using a modular glucose measuring module and insulin pump combination, comprising:
   (a) attaching a glucose measuring module without a display to an insulin pump housing with a mechanical clasp comprising a quick attach and release mechanism in a single action;
   (b) inserting a glucose test strip in the module;
   (c) contacting the glucose test strip to a blood sample;
   (d) determining data relating to a glucose value based on said sample using a microprocessor in the module;
   (e) transmitting said data wirelessly from said module to said insulin pump and converting said data to a glucose value using a microprocessor in said pump;
   (f) displaying said glucose value on a display on said pump; and
   (g) detaching the clasp and module from the pump housing in a single action.

8. A method as in claim 7, wherein the attaching comprises engaging a lip of the quick attach and release mechanism with a lip-engaging portion of the pump housing to align the insulin pump housing with the glucose measuring module.

9. The method of claim 7 including activating the glucose measuring module when the glucose test strip is inserted.

10. The method of claim 9 wherein activating the glucose measuring module includes transmission of a signal to the insulin pump.

11. The method of claim 10 wherein the signal is displayed on the display of the pump indicating activation of the glucose measuring module.

12. The method of claim 7 including controlling one or more functions of the glucose measuring module using a control button provided on the insulin pump housing.

13. A method of measuring the glucose level of a diabetic using a modular glucose measuring module and insulin pump combination, comprising:
   (a) attaching a glucose measuring module without a display to an insulin pump housing using a mechanical clasp comprising a quick attach and release mechanism;
   (b) inserting a glucose test strip in the module;
   (c) contacting the glucose test strip to a blood sample;
   (d) determining data relating to a glucose value based on said sample using a microprocessor in the module;
   (e) transmitting said data wirelessly from said module to said insulin pump and converting said data to a glucose value using a microprocessor in said pump;
   (f) displaying said glucose value on a display on said pump; and
   (g) detaching the clasp and module from the pump housing.

14. The method of claim 13, wherein the glucose measuring module is attached to the insulin pump housing in a single action, and further, wherein the insulin pump housing is detached from the glucose measuring module in a single action.

15. The method of claim 14, wherein the attaching comprises engaging a lip of the quick attach and release mechanism with a lip-engaging portion of the pump housing to align the insulin pump housing with the glucose measuring module.

16. The method of claim 13, wherein attaching the glucose measuring module to the insulin pump housing aligns a data communication port of the glucose measuring module to a data communication port on the insulin pump housing.

17. The method of claim 16, wherein the data communication port of the glucose measuring module and the data communication port of on the insulin pump housing includes an infrared (IR) data transmission port, respectively.

18. The method of claim 13 including activating the glucose measuring module when the glucose test strip is inserted.

19. The method of claim 18 wherein activating the glucose measuring module includes transmission of a signal to the insulin pump.

20. The method of claim 19 wherein the signal is displayed on the display of the pump indicating activation of the glucose measuring module.

21. The method of claim 13 including controlling one or more functions of the glucose measuring module using a control button provided on the insulin pump housing.

* * * * *